United States Patent [19]

Reese

[11] 4,108,976

[45] Aug. 22, 1978

[54] AUTOMATED DIRECT SERUM RADIOIMMUNOASSAY

[75] Inventor: Max G. Reese, Salt Lake City, Utah

[73] Assignee: Becton, Dickinson and Company, East Rutherford, N.J.

[21] Appl. No.: 774,390

[22] Filed: Mar. 4, 1977

[51] Int. Cl.² .................... A61K 43/00; G01N 33/16; G01N 23/00
[52] U.S. Cl. .................................... 424/1; 23/230 B; 23/253 R; 424/12
[58] Field of Search ............ 23/253 C, 230 B; 424/1, 424/12

[56] References Cited

U.S. PATENT DOCUMENTS

| | | | |
|---|---|---|---|
| 3,896,217 | 7/1975 | Johnson | 424/1 |
| 3,940,475 | 2/1976 | Gross | 424/1 |
| 3,950,134 | 4/1976 | Miles | 23/230 B |
| 3,950,643 | 4/1976 | Charlton | 424/1 X |
| 3,989,383 | 11/1976 | Paulson | 23/230 B X |
| 4,009,005 | 2/1977 | Johnson | 23/253 R |
| 4,022,577 | 5/1977 | Brooker | 23/230 B |

Primary Examiner—Benjamin R. Padgett
Assistant Examiner—Christine M. Nucker
Attorney, Agent, or Firm—Mario A. Martella

[57] ABSTRACT

Automated radioimmunoassay directly from serum, for those antigens present in serum in relatively small amounts, is accomplished by use of an immobilized immunoadsorbent having an excess of antibodies, specific to the antigen, covalently bonded to a particulate substrate. The serum is diluted and preincubated in the presence of a radioactive labelled antigen and an antibody specific to the antigen. The preincubated mixture is flowed through the immobilized immunoadsorbent and the labelled and unlabelled antigen not bound to the antibody in preincubation are bound to the immobilized immunoadsorbent while the labelled and unlabelled antigen bound to the antibody during preincubation flow through the immunoadsorbent. An eluting solution is flowed through the immunoadsorbent to release the antigens bound thereto for reuse of the immunoadsorbent. By counting the radioactivity of one or both the fractions which flow through the immunoadsorbent or which is released therefrom, the quantity of a specific antigen in the serum may be assayed.

10 Claims, No Drawings

AUTOMATED DIRECT SERUM RADIOIMMUNOASSAY

BACKGROUND OF THE INVENTION

This invention relates to radioimmunoassay and more specifically to an improved method for the direct assay of antigens such as triiodothyronine ($T_3$), in serum by the use of an immobilized immunoadsorbent.

STATE OF THE ART

Radioimmunoassay is an analytical technique which depends upon the competition (affinity) of antigen for antigen-binding sites on antibody molecules. In practice, standard curves are constructed from data gathered from a plurality of samples each containing (a) the same known concentration of labelled antigen, and (b) various, but known, concentrations of unlabelled antigen. Antigens are labelled with a radioactive isotope tracer. The mixture is incubated in contact with an antibody, the free antigen is separated from the antibody and the antigen bound thereto, and then, by use of a suitable detector, such as a gamma or beta radiation detector, the percent of either the bound or free labelled antigen or both is determined. This procedure is repeated for a number of samples containing various known concentrations of unlabelled antigens and the results plotted. The percent of bound tracer antigens is plotted as a function of the antigen concentration. Typically, as the total antigen concentration increases the relative amount of the tracer antigen bound to the antibody decreases. After the standard graph is prepared, it is thereafter used to determine the concentration of antigen in samples undergoing analysis.

In actual analysis, the sample in which the concentration of antigen is to be determined is mixed with a known amount of tracer antigen. Tracer antigen is the same antigen known to be in the sample but which has been labelled with a suitable radioactive isotope. The sample with tracer is then incubated in contact with the antibody. Thereafter, it may be counted in a suitable detector which counts the free antigen remaining in the sample. The antigen bound to the antibody or immunoadsorbent may also be similarly counted. Then, from the standard curve, the concentration of antigen in the original sample is determined. Afterwards, the antibody or immunoadsorbent mass is discarded.

In order to detect the percentage of antigen that is bound to the antibody (bound antigen) and/or the percentage that remains free or unbound it is necessary to first separate the sample into a fraction containing bound antigen and one containing only free antigen. One common method for doing this is to add a dextran coated charcoal to the mixture. The dextran permits the unbound antigen, of lower molecular weight than the bound antigen, to pass through the dextran and the charcoal adsorbs the free antigen. The charcoal with adsorbed free antigen is then separated from the antibody (and bound antigen) by centrifugation.

Another known procedure is to add to the mixture another antibody which selectively precipitates the first antibody (with the bound antigen) thus leaving in solution only free antigen. Classification into appropriate free and bound fractions is then effected by separating the precipitate from the supernatant by centrifugation or other suitable means. Some workers have resorted to the technique of binding the antibody to the inner walls of a plastic vessel, filling the vessel with the antigen bearing sample, allowing it to stand for an incubation period that typically ranges from 4 to 72 hours and then separating free antigen from bound antigen by draining and rinsing the vessel leaving therein only the antibody and bound antigen. A more recently developed technique is to prepare the immunoadsorbent by binding the antibodies onto an insoluble cross-linked dextran. The immunoadsorbent and antigen bearing sample are incubated then the dextran with bound antigen is separated from the solution by suitable means.

In all of the foregoing procedures, the percentage of labelled antigen in either or both the bound or free fractions is determined and the standard curve used to determine the antigen concentration. Thereafter, the immunoadsorbent is discarded.

Although the foregoing radioimmunoassay techniques have proven to be valuable tools and have gained widespread acceptance, they are still not all that are to be desired because the antibody (immunoadsorbent) is consumed with each analysis hence must be discarded. Moreover, prior practice is batch type and the several reagents are added to the antibody in test tubes in which the separate steps, such as incubation, rinsing and the like, are performed, thus resulting in a slow and costly operation.

An improvement of the above described prior procedure is set forth in U.S. Pat. No. 3,896,217 of July 22, 1975, assigned to the same assignee. There, an immobilized immunoadsorbent having covalently bound antibodies is used to bind antigen, followed by release of antigen by flowing an eluting solution through the immunoadsorbent. By this system, the immunoadsorbent may be reused repeatedly.

An automated apparatus is described in U.S. Ser. No. 565,850, filed Apr. 7, 1975, as a continuation-in-part of U.S. Pat. No. 3,896,217 setting forth in more detail the various aspects of the equipment for automated radioimmunoassay by the use of a reusable immobilized immunoadsorbent.

Application Ser. No. 565,848, filed Apr. 7, 1975, describes an improved immunoadsorbent and methods of making and using the same. As there described, the immunoadsorbent includes a particulate substrate having bonded thereto by covalent bonds the antibody specific to the antigen.

Since the systems of the above patents and applications relate principally to a flow-through type of system, one of the practical aspects of the technology is the flow-through character of the various mixtures which pass into and through the immobilized immunoadsorbent. More particularly, if the materials flowing through the immobilized immunoadsorbent, usually placed in a chamber, tend to plug up the flow passages, the use and reuse of the chamber is adversely affected. Such adverse effects are manifest in several different ways including physically plugging to prevent flow and thus interference with subsequent tests by trapping labelled and unlabelled antigen in the column, or by slowing the flow through the chamber sufficiently to extend unreasonably the time for what should be a relatively rapid automative assay, or both.

As will be appreciated, plugging is a characteristic only of those immunoadsorbents which are reusable. With single use immunoadsorbents, to be discribed, the flow through and repeated flow through of material is not of major consequence.

One source of plugging are the proteins, other than the antigen, which may be present in a sample. While the chamber includes a screen to filter out large components, the proteins may pass through the screen and accumulate in the interstices of the particulate substrate especially if that substrate is of the type described in U.S. Pat. No. 3,505,785 of A.pr. 14, 1970, a substrate which is desirable because each particle is a macroparticle with an impervious core having a coating of monolayers of colloidal microparticles thereby providing a substantial surface area.

A typical source of plugging proteins is serum, i.e. blood from which suspended cellular elements have been removed usually by centrifugation. Thus, if undiluted serum is assayed using an immunoadsorbent of the type described in the above referenced patent and patent applications, the relatively large proteins pass through the filter and tend to plug up the immunoadsorbent. The serum may be diluted to reduce the concentration of proteins for better flow through the immunoadsorbent. Dilution, however, also reduces the concentration of the antigens in the serum. Where the concentration of free antigen in serum is relatively low, e.g. digoxin and $T_3$, diluting the serum reduces the concentration even more and presents problems in accurately and reliably assaying for the relatively small amounts of antigen present in the diluted serum. Thus, dilution to avoid a plugging problem leads to problems of accurate assays, i.e. the sensitivity of the assay is less than desired.

DESCRIPTION OF THE PRIOR ART

It is known from the literature that antibodies may be isolated by use of immunologic adsorbents, the technique being useful for isolation and purification of antibodies rather than quantitative determination thereof, see Campbell et al, *Proc. Nat'l. Acad. Sci.* U.S. 37 (1951) 575.

The use of an antibody coupled to an insoluble polymer for extracting specific antigens for purposes of isolating and purifying the same is described in Weetall et al, *Biochem. Biophys. Acta.* 107 (1965) 150–152.

Porous glass has been described as a substrate for immobilizing enzymes, see Weetall, *Biochem. Biophys. Acta.* 212 (1970) 1–7. There, glass was treated with gammaaminopropyltriethoxysilane and the isothiocyanate derivative was prepared by treatment with thiophosgene. The enzyme was coupled to the isothiocyanate derivative. Also described in the preparation of an arylamine derivative by the reaction of alkylamine glass with P-nitrobenzoyl chloride followed by use of sodium dithionate to reduce the nitro groups. The arylamine glass was then diazotized and the enzyme coupled thereto.

Weetall, in *Biochem. J.* (1970) 117, 257–261 also describes the use of antibodies bound to porous glass through a silane coupling agent, the immunoadsorbent being used to isolate and purify specific antigens. The data given, however, shows that the reused column, in which the antigen was eluted from the immobilized antibody immunoadsorbent was quite erratic in performance since the recovery of released antigen varied from 74% to 100%. See also U.S. Pat. No. 3,652,761 of Mar. 28, 1972. While useful as an isolation system, the described system has considerable objections from the standpoint of a useable tool in quantitative analysis in which there must be substantially stoichiometric release of the antigen.

U.S. Pat. No. 3,555,143 of Jan. 12, 1971, relates to radioimmunoassay procedures in which an immobilized immunoadsorbent is used only once and then discarded. The immunoadsorbent is a dextran (Sephadix G 25, superfine) cross-linked with glycerine ether bridges and substituted with p-nitrophenoxy-hydroxy-propyl ether groups. The nitro groups are reduced to amine groups using sodium dithionite. The Sephadex substituted with p-amino-phenoxy-hydroxy-propyl groups was then treated with thiophosgene to form Sephadex substituted with p-isothiocyanate-phenoxy-hydroxypropyl groups, the antibody being bound to the latter substituted product.

A reaction widely used to insolubilize a protein involves a covalent binding of the protein to a cyanogen bromide activated cellulose matrix. The mechanism of such activation is set forth in Bartling et al, *Biotechnology and Bioengineering*, Vol XIV (1972) 1039–1044.

U.S. Pat. Nos. 3,502,888 of July 13, 1971; 3,639,559 of Feb. 1, 1972, and 3,720,760 of Mar. 13, 1972, are also of interest.

Where an immobilized immunoadsorbent is to be used only once and discarded, the long term properties of the substrate are not of major consequence. Thus, materials such as Sephadex (dextran) or Sepharose (beaded agarose product) operate satisfactorily as substrates for antibodies bound thereto as described in U.S. Pat. No. 3,555,143, supra.

One of the objections is the tendency of Sephadex and Sepharose type products to dehydrate, that is, the gel collapses and packs to such an extent that flow through the mass is substantially impeded and the availability of antibody for binding antigen is altered, thus effecting the reproducibility and stability of the immunoadsorbent for repeated use.

Glass and other solid inorganic materials offer a desirable alternative because they can be formed into beads to provide better flow and easier packing into a column type arrangement. Such materials do not collapse and are not subject to dehydration during periods of extended use. While a desirable alternate, glass type products also suffer from disadvantages. One of the problems is obtaining a sufficient binding of the antibody to the substrate. Either an insufficient initial binding takes place to provide the activity needed for a quantitative analysis tool, or the activity changes over the life of the immunoadsorbent by undesirable release of antibodies.

Where the glass is highly porous, as that used by the Weetall references cited, there is so much active glass surface area that ample binding of the antibody takes place but non-specific binding of the antigen also takes place. Thus, the antigen bound to the glass is not released completely. That is, rather than having a stoichiometric release, for each use thereof, as is needed for quantitative analysis, the release characteristics are variable and unpredictable. This is confirmed by the Weetall data. Since such glass is usually 96% air or void space, there is considerable active surface area of the glass, not occupied by antibody which serves as an antigen binding site.

Another difficulty with highly porous glass products is that there are multiple crevices in the pores which result in trapping in the crevices and slow release because of the slow diffusion in the crevices. Where a fast response is needed, as for example in automated equipment, the diffusion of the reactants is a rate limiting step and, as is well known, diffusion may be a relatively slow process. Thus, even if not bound to the substrate, the diffusion of the antigen is relatively slow and thus, for the purpose of rapid automated assay equipment, the antigen is effectively bound rather than being rapidly and stoichiometrically released.

U.S. Pat. No. 3,793,445, of Feb. 19, 1974, describes an immunoadsorbent which is a polyacrylamide gel matrix which physically entrap the antibody in a matrix of controlled pore size are subject to hydration by the eluting solvent. Thus, after elution, the gel entrapped immunoadsorbent is rinsed with a buffer, dehydrated with acetone, dried in air and then reused. The post elution treatment of the gel needed to eliminate the effects of gel hydration tend to increase the cycling time unreasonably as compared to an immunoadsorbent in which the antibody is covalently coupled to a particulate substrate which is not subject to hydration.

U.S. Pat. No. 3,911,096 of Oct. 7, 1975, relates to the method of measuring $T_3$ and $T_4$ from unextracted serum by displacing $T_3$ and $T_4$ from thyroxine or triiodothyronine binding globulin (TBG) by the use of a blocking agent, of which several examples are given. Other than the use of a blocking agent, the procedure is a conventional radioimmunoassay in which separation of a bound and free fraction formed during incubation is accomplished by a precipitation procedure.

SUMMARY OF THE INVENTION

Thus the present invention offers singular advantages over the prior patents, applications and literature references and prior procedures referred to above. In brief, the system of the present invention permits automatic radioimmunoassay from serum, at room temperature, while assuring proper flow through an immobilized immunoadsorbent including a particulate substrate to which antibodies are covalently bound. This is achieved while maintaining assay sensitivity, i.e. accuracy of assay at low levels of antigen.

Thus, radioactive tracer labelled antigen and unlabelled diluted serum sample (or standard) antigen is preincubated with specific antibody in a sample cup for a period of 30 minutes to 3 hours or more. Separation of free and bound antigen is accomplished on the equipment described in U.S. Ser. No. 565,850 previously identified. The antibody chamber includes an immobilized immunoadsorbent composed of a particulate solid substrate to which excess specific antibody is covalently attached. The sample containing free antigen and antigen bound to the antibody, as a result of the preincubation step, is passed through the antibody chamber. Since the serum sample has been diluted, the concentration of proteins tending to plug the chamber is reduced and there is satisfactory free flow of the sample through the chamber.

During flow through the immobilized immunoadsorbent, the free antigen (labelled and unlabelled) binds to the antibody bound to the support while the bound antigen, i.e. the labelled and unlabelled antigen bound to the antibody in the preincubation step, passes through the chamber to a radioactive detector where it is counted. Subsequently, an eluting solution is flowed through the chamber and the immunoadsorbent to free the antigen bound to the antibody immobilized on the immunoadsorbent. The antigen (labelled and unlabelled) freed from the immunoadsorbent by the eluting solution flows to a radioactive detector where it is counted. Following elution to free the antigen, the immunoadsorbent is rinsed and ready for reuse in the next and subsequent cycles.

By diluting the serum the problems of flow are substantially reduced in the sense that the material flowing through the chamber does not plug the chamber or the immobilized immunoadsorbent. Dilution, however, reduces the concentration of the antigens and thus creates sensitivity problems especially at the low concentration range of those antigens which are present in serum at low concentrations to begin with. By this invention, it has been discovered that sensitivity can be increased by the preincubation step which requires that substantially all the free antigen be separated by attachment to the antibody covalently bound to the support. Thus, the immunoadsorbent includes an excess of specific antibody to assure that the free antigen is "captured".

In order that the invention may be more readily understood and carried into effect, reference is made to the accompanying description which is offered by way of illustration and not in limitation of the invention, the scope of which is defined in the appended claims.

DETAILED DESCRIPTION OF PREFERRED EMBODIMENTS

There are advantages, from a practical standpoint, in the provision of a system for automated radioimmunoassay, at room temperature, directly from serum. Thus, in accordance with this invention, the general sequence includes a preincubation step followed by a separation and counting operation to determine the quantity of a selected antigen present in the serum.

As will be appreciated, the quantity of antigen in a sample is related to standards of known concentration which are assayed to develop standard curves against which unknowns are compared. This may be done by computer as explained in U.S. Ser. No. 565,850 to which reference has been made. The generation of data from standards is accomplished by the same basic sequence used with unknowns. Accordingly, in the following discussion reference will be made to "sample" i.e. the antigen sample of unknown concentration, and to "standard" the sample of antigen of known concentration.

A known amount of radioactive labelled tracer antigen is admixed with a sample or standard and preincubated in the presence of an antibody specific to that antigen. This may be carried out in a polystyrene sample cup of about 2 ml total volume.

The preincubation time may vary but is normally in the range 30 minutes to 3 hours or more, at room temperature. During the preincubation, a portion of each of the labelled and unlabelled antigen sample or standard is bound to the antibody, while the remainder of the labelled and unlabelled antigen is free. This mixture is then flowed through an immobilized immunoadsorbent, to be described, to effect separation of the labelled and unlabelled antigen bound to the antibody in the preincubation step and the labelled and unlabelled antigen which is free.

During flow through of the immunoadsorbent, the free fraction binds to the antibody which is immobilized on the substrate and the bound fraction (labelled and unlabelled antigen and bound to antibody during preincubation) flows through the immunoadsorbent which may then be counted for radioactivity. Thereafter, the free fraction bound to the immobilized immunoadsorbent is freed by flowing an eluting solution through the immunoadsorbent to effect stoichiometric release of the fraction bound to the immobilized immunoadsorbent. The free fraction may then be counted for radioactivity. Standard data, in the case of standards, or determination of the amount of the sample by comparison with standard data may be generated from the counts, as is well known in the art.

Following elution, the immunoadsorbent is rinsed and is reused for further assays of the same antigen.

The immunoadsorbent may be placed in a chamber and may be of the type described in U.S. Ser. No. 564,848, to which reference has been made. Alternately, the immobilized immunoadsorbent may be of the type set forth in U.S. application Ser. No. 774,227 filed of even date herewith and assigned to the same assignee. Regardless of the specific form of the immobilized immunoadsorbent, it preferably includes a particulate solid substrate, stable against hydration, and having antibodies covalently bonded thereto. Various techniques have been described in the pending application herein referred to by which antibodies may be covalently bound to a solid particulate support. With these types of immobilized immunoadsorbents, the bond between the antigen and the antibody bound to the support is broken by the eluting solution which does not adversely affect the covalent bond by which the antibody is bound to the support. Accordingly, the free antigen is stoichiometrically released and the immunoadsorbent may be reused repeatedly.

The repeated reuse of the immunoadsorbent and the particulate nature of the substrate creates problems of flow through if there are materials in the mixture which plug up the immunoadsorbent. One source of plugging components is the proteins present in serum. While these relatively large proteins may not present problems in a single use of an immunoadsorbent, where the immunoadsorbent is to be repeatedly reused, as is the case in an automated radioimmunoassay system contemplated by this invention, these proteins may create problems.

Thus in accordance with this invention, the serum sample is diluted, but in doing so there may be dilution of some of the antigens to such a low level that accurate assay therefor is quite difficult in an automated system whose entire purpose is to perform the assay reliably and in a relatively short time.

Typical antigens which are present in serum in small amounts are triiodothyronine ($T_3$) and digoxin, for example. By way of illustration, $T_3$ may be present in a range of .25 to 0.8 ng/ml of serum (hypo condition), 0.8 to 1.3 ng/ml of serum (normal condition), and 1.3–2.0 ng/ml of serum (hyper condition). Dilution of serum to reduce the concentration of plugging proteins also reduces the concentration of $T_3$. This renders it difficult to assay for the lower levels of $T_3$ if the serum initially has $T_3$ present only in the lower level. Thus the sensitivity, at relatively low levels of $T_3$ is adversely affected by serum dilution.

By the present invention, the sensitivity of the assay for $T_3$ in diluted serum is 10 picograms/ml, i.e. 0.1 ng/ml of serum.

This sensitivity in an automated assay from serum and at room temperature is achieved by a preincubation of the diluted sample with an antibody and a known amount of labelled antigen. The preincubation, in effect, prebinds a portion of the antigen in the sample. The preincubation is conducted for a period of time sufficient to establish an equilibrium condition, usually 30 minutes 3 hours or more. Preincubation may be conducted on an automated basis by known automated pipetting equipment. This aspect of the assay is in the nature of pretreating of the samples or standards to allow for the assay rapidly and reliably.

The separation, conducted automatically and quickly, involves flowing the mixture formed during preincubation through an immunoadsorbent which has the same kind of antibody bound to the support as was used in the preincubation, except that there is an excess of antibody. Effectively, the immunoadsorbent has an activity which binds 80% or more based on the amount of antigen in the serum, an excess which is substantially greater than the amount of free antigen present in the preincubated mixture. Thus, a significant amount, e.g., 80% or more, of the free antigen passing through the immunoadsorbent is bound to the antibody bound to the substrate.

The free fraction passing through and the fraction freed by elution may be counted as described.

Thus, one aspect of the present invention is that binding on the immunoadsorbent is relatively rapid even though the preincubation, or initial binding phase, is comparatively slow. In a typical example for the assay of $T_3$, reagents were prepared as follows:

(a) The adsorption buffer used to introduce the sample was 0.05 M tris-HCl buffer, pH 9.2 containing 0.01% (W/V) bovine serum albumin.

(b) The eluting solution was 60% methanol in 0.01M sodium phosphate buffer, pH 7.5.

(c) The rinse solution was 50% methanol in 0.01M sodium phosphate buffer, pH 7.5.

(d) The sample buffer was 0.05 M tris-HCl, 0.01% (W/V) bovine serum albumen, 160 microgram/ml of 8-anilino naphthalene — 1 sulfonic acid (Na salt) (ANS), and 45 nC/ml $^{125}$I labelled $T_3$ antigen, specific activity 3,000 mC/mg. Thus the sample buffer contains a known amount of labelled antigen.

Thyroid hormone free serum was prepared by stirring activated charcoal with the serum for 18 hours. The charcoal was removed by centrifugation followed by filtration of the serum through a 0.4 micron filter.

The charcoal removes the $T_3$ binding proteins which may compete with the $T_3$ antisera. Thus, the concentration of binding proteins may be restored by using more thyroid hormone free serum for the standards.

Standard solutions were prepared as follows:

Aqueous standards of known concentrations varying from 3.9 to 1000 picogram/ml were prepared in aliquots of sample buffer, (d), supra. To each 1.0 ml of aqueous standard there was added 50 microliters of thyroid hormone free serum to restore the concentration of binding proteins.

The antibody solution was prepared using $T_3$ specific antibody raised in rabbits against triiodothyroproprionic acid conjugated to rabbit serum albumen. One microliter of antisera was diluted into 1 ml of adsorbtion buffer, (a), supra.

The filter used for preparation of the thyroid free hormone serum was a standard antibody chamber as described in United States application Ser. No. 565,848, filed Apr. 7, 1975, assigned to the same assignee, and whose disclosure is incorporated herein by reference. The lower support, or filter outlet, consists of a nylon mesh (400) disc, Teflon wool disc and nylon mesh (400) disc. The body of the chamber was filled with glass wool.

The antibody chamber used in the assays is as described in Ser. No. 565,848, wherein the lower support, or exit end of the chamber, consists of nylon mesh (400) disc, a Teflon felt disc and a nylon mesh (400) disc.

Antibody to $T_3$ conjugated to cyanogen bromide activated dextran coated Zipax was added to fill the chamber compartment. The upper support was a single Teflon felt disc.

Assays were conducted using the automated equipment as described in United States application Ser. No. 565,850, filed Apr. 7, 1975, assigned to the same assignee, and whose disclosure is incorporated herein by reference. The buffer pump speed was 1.00 ml/min.

In practice, assays involve generation of data from standard solutions using a specific antibody chamber, followed by assays of unknowns using the same chamber and reagents and process times used for the standards. The sequence involves adding to each 1.0 ml of standard solution (prepared above) in a polystyrene sample cup, 0.1 ml of diluted (1:1,000) $T_3$ antisera, prepared as described. The total volume of the sample cup was 2 ml. The mixture was incubated, covered, and in the dark for at least three hours at room temperature.

Unknowns were prepared for analysis by diluting 40 microliters of unknown serum with 1.0 ml of sample buffer in a serum cup, to which was added 0.1 ml of diluted $T_3$ antisera, prepared as described. The dilution of the unknown was 26 fold while the dilution of the standard was 21 fold. Following incubation of the unknown with the antibody, the free and bound antigen may be separated and counted using the automated equipment.

The labelled antigen is present in the sample buffer in a known amount. The reactions during an assay of a standard or unknown may be understood using the following symbols:

$Ag^*$ is labelled antigen; $Ag(S \text{ or } U)$ is the standard or unknown unlabelled antigen; $Ab$ is the antibody; and $SS_{ab}$ is the immunoadsorbent. The sequence may be represented as follows:

In the sample cup (preincubation):

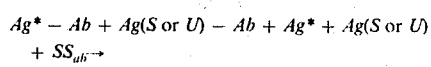

$$Ag^* - Ab + Ag(S \text{ or } U) - Ab + Ag^* + Ag(S \text{ or } U)$$

In the presence of the immobilized immunoadsorbent, the mixture resulting from preincubation forms two fractions, a free fraction (underlined) and a bound fraction, as follows:

$$Ag^* - Ab + Ag(S \text{ or } U) - Ab + Ag^* + Ag(S \text{ or } U) + SS_{ab} \rightarrow$$

$$Ag^* - SS_{ab} - Ag(S \text{ or } U) + Ag^* - Ab + Ag(S \text{ or } U) - Ab$$

The bound fraction is pumped to the detector for counting and thereafter the free fraction is eluted from the antibody covalently bound to the solid support, as indicated in the following:

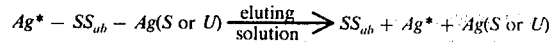

The released antigen is also pumped to the detector for counting.

Using the above described procedures, four clinical samples were run along with two sets of commercial serum control samples. Data from standards were also generated, as shown in the following table.

|  | $T_3$ DATA | | | | | |
| --- | --- | --- | --- | --- | --- | --- |
|  | Free | Bound | Total | % Bound(7) | Assay pg/ml(8) | Serum pg/ml |
| Blank (1) | 436 | 527 |  |  |  |  |
| Blank (2) | 4082 | 2805 | 5924 | 38.5 |  |  |
| Standard - 3.9 (3) | 3964 | 2908 | 5909 | 40.3 |  |  |
| Standard - 7.8 | 3712 | 3084 | 5833 | 43.8 |  |  |
| Standard - 15.6 | 3713 | 3297 | 6047 | 45.8 |  |  |
| Standard - 31.2 | 3216 | 3646 | 5899 | 52.9 |  |  |
| Standard - 62 | 2684 | 4302 | 6023 | 62.7 |  |  |
| Standard -125 | 2194 | 4573 | 5804 | 69.7 |  |  |
| Standard - 250 | 1688 | 5183 | 5908 | 78.8 |  |  |
| Standard - 500 | 1496 | 5417 | 5950 | 82.2 |  |  |
| Standard - 1000 | 1306 | 5364 | 5707 | 84.8 |  |  |
| Blank (1) | 529 | 568 |  |  |  |  |
| Blank (2) | 4267 | 2781 | 6085 | 37.0 |  |  |
| Clinical (High) (4) | 3060 | 2851 | 5959 | 56.0 | 40 | 1040 |
| Clinical (Low) | 3491 | 3628 | 6156 | 50.4 | 24 | 624 |
| Clinical (High) | 2950 | 4186 | 6173 | 59.3 | 50 | 1300 |
| Clinical (Low) | 3567 | 3680 | 6284 | 50.2 | 24 | 624 |
| Commercial (Low) | 2995 | 3046 | 6078 | 41.4 | 5 | 130 |
| Commercial (Normal) | 3494 | 3570 | 6101 | 49.9 | 21 | 546 |
| Commercial (High) | 2605 | 4536 | 6178 | 64.9 | 76 | 1976 |
| Commercial (5) | 3385 | 3848 | 6270 | 53.0 | 32 | 832 |
| Commercial (6) | 2283 | 4701 | 6021 | 69.3 | 110 | 2860 |

(1) The blank contained no radioisotope but merely the components of the sample buffer less the labelled antigen. This blank provided background counts.

(2) This blank was the sample buffer without unlabelled $T_3$.

(3) Standard concentration expressed in picograms of $T_3$/ml.

(4) Clinical samples were of unknown concentration, but in the general ranges indicated.

(5) Commercial sample of a concentration of 700 pg $T_3$/ml ± 200.

(6) Commercial sample of a concentration of 2,500 pg $T_3$/ml ± 400.

(7) Calculated by subtracting the free and bound background counts from the free and bound net counts.

(8) Expressed in terms of percentage of antigen bound to the antibody covalently coupled to the solid support.

From the above data, it can be seen that there is good correlation between the determination made in accordance with the present invention, by automated equipment, and the actual concentration.

The above data also indicate the sequence used for generation of data from the standards, all of which are processed by the same procedure, and the same procedure used for the unknowns which include both the clinical and commercial samples.

The advantage of the present invention is the ability to provide relatively rapid and accurate determinations directly from serum for antigens present in relatively small amounts by the use of automated equipment. The preincubation sequence not only reduces on machine time, but permits dilution of the serum so as to reduce substantially the concentration of plugging proteins present in serum. By use of preincubation, the sensitivity of the assay is increased substantially to the point where the antigens present in small amounts may be assayed accurately by a flow through system, as described.

On aspect of the present invention is the provision of an immunoadsorbent in which the amount of covalently bound antibody is in excess of the free unbound labelled and unlabelled antigen which is not bound during the preincubation sequence. Unlike prior disclosed procedures using a solid immunoadsorbent in which only a portion of the antigen (labelled and unlabelled) is bound by the immobilized antibody on the substrate, the preferred procedure of the present invention involves binding to the substrate substantially all of the labelled and unlabelled antigen which is not bound to the antibody during the preincubation sequence. Thus, the binding activity of the solid immunoadsorbent is such that it is at least 80% or more based on the amount of antigen in the sample to be assayed.

For example, based on the data given in the Table, the immunoadsorbent should have sufficient binding activity to bind 2850 pg/ml of $T_3$. Unlike the immobilized immunoadsorbents previously disclosed, the immobilized immunoadsorbent useable in accordance with the present invention has a binding activity which is quite high based on the anticipated antigen concentration in the sample. As a practical matter, the binding activity of the immunoadsorbent may be several times the anticipated concentration of the samples in order to provide assurance that substantially all of the labelled and unlabelled antigen not bound in the preincubation sequence are bound during flow through the immunoadsorbent.

It has been noted that antigens such as triiodothyronine and tetraiodothyronine tend to deposit on the surfaces of the various flow lines through which they flow, especially if the flow lines are of plastic material. The accumulation of $T_3$ or $T_4$ in the system may adversely affect the sensitivity of the procedure. Thus, in accordance with this invention, a rinse solution is used, after each assay, which releases any $T_3$ or $T_4$ which may tend to deposit.

A typical material useable as a rinse solution is 2% solution (by weight) of dimethylammonium linear dodecyl benzene sulfonate (DMS) in a 30% solution (by volume) of methanol in water or 1% DMS in water.

While the above invention has been described with reference to $T_3$, it will be understood that the procedures herein described have applicability to those instances in which the antigen is present in relatively small amounts and with proteins which tend to create flow problems through a solid substrate immunoadsorbent, especially if the immunoadsorbent is rinsed.

It will also be apparent to those skilled in the art that various modifications and alternatives may be made without departing from the spirit and scope of the invention as set forth in the appended claims.

I claim:

1. In a process for automated radioimmunoassay of an antigen sample by flowing the sample through a chamber containing an immobilized immunoadsorbent composed of particulate substrate having antibodies specific to the antigen covalently bound thereto, and wherein the sample contains proteins tending to plug up the particulate substrate, the improvement comprising:

diluting the sample to a consistency for free unplugged flow through the immobilized immunoadsorbent, preincubating the sample with an antibody specific to the antigen in said sample being assayed together with a known amount of a radioactive labelled antigen to form a mixture including
(a) unlabelled antigen bound to the antibody,
(b) labelled antigen bound to the antibody,
(c) free unbound unlabelled antigen, and
(d) free unbound labelled antigen;

providing a chamber containing an immobilized immunoadsorbent including a solid particulate substrate having covalently bound thereto an antibody specific to said antigen and in an amount in excess of the sum of the free unbound labelled and unlabelled antigen, flowing said mixture through said chamber to form two fractions, one of which is the free unbound labelled and unlabelled antigen bound to the antibody on said substrate and the second being the labelled and unlabelled antigen bound to the antibody during the preincubation step, whereby said second fraction passes through said chamber and said first fraction binds to the immobilized immunoadsorbent, flowing an eluting solution through said chamber to effect release of said first fraction, counting the radioactivity of at least one or both of the fractions leaving said chamber as a function of the quantity of the antigen sought to be assayed in said sample and rinsing the chamber for subsequent assays of other samples of the same antigen.

2. In a process as set forth in claim 1 wherein said sample is serum containing proteins tending to plug said chamber.

3. In a process as set forth in claim 1 wherein the binding activity of said immobilized immunoadsorbent is not less than 80% of the concentration of the antigen in the sample.

4. In a process as set forth in claim 2 wherein the steps are carried out at room temperature.

5. In a process as set forth in claim 1 wherein said preincubation is conducted for a period of time sufficient to establish an equilibrium between the labelled and unlabelled antigen bound to the antibody and the free and unbound labelled and unlabelled antigen.

6. A process for the direct radioimmunoassay of $T_3$ antigen in a serum sample comprising the steps of preincubating an antibody specific to $T_3$ antigen in the presence of radioactive labelled $T_3$ antigen and unlabelled $T_3$ antigen sample to form a mixture including
(a) unlabelled antigen bound to the antibody,
(b) labelled antigen bound to the antibody,
(c) free unbound unlabelled antigen, and (d) free unbound labelled antigen;

passing said mixture through a chamber containing an immobilized immunoadsorbent including a solid particulate substrate having an amount of antibodies covalently bound to said support which is in excess of the amount of the sum of the free unbound labelled and free unbound unlabelled antigen to effect binding of the free unbound labelled and unlabelled antigen to the immobilized immunoadsorbent while said labelled and unlabelled antigen bound to said antibody passes through said chamber, flowing an eluting solution through said chamber to effect release of the labelled and unlabelled antigen bound to said immobilized immunoadsorbent, counting the radioactivity of at least one of the labelled and unlabelled antigen bound to said antibody and the labelled and unlabelled antigen released from the immobilized immunoadsorbent as a function of the quantity of antigen in said serum.

7. In a process as set forth in claim 6 wherein the binding activity of said immobilized immunoadsorbent is not less than 80% of the concentration of the antigen in said serum sample.

8. In a process as set forth in claim 6 wherein 80% or more of the free unbound labelled and unlabelled antigen flowed through said chamber is bound to the immobilized immunoadsorbent.

9. In a process as set forth in claim 8 wherein the steps are carried out at room temperature.

10. In a process as set forth in claim 7 wherein the preincubation is conducted for a period of time sufficient to establish an equilibrium between the labelled and unlabelled antigen bound to the antibody and the free and unbound labelled and unlabelled antigen.

* * * * *